(12) United States Patent
Miga

(10) Patent No.: US 10,743,941 B2
(45) Date of Patent: Aug. 18, 2020

(54) METHOD AND SYSTEM FOR TRACKERLESS IMAGE GUIDED SOFT TISSUE SURGERY AND APPLICATIONS OF SAME

(71) Applicant: Vanderbilt University, Nashville, TN (US)

(72) Inventor: Michael I. Miga, Franklin, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 525 days.

(21) Appl. No.: 15/359,801

(22) Filed: Nov. 23, 2016

(65) Prior Publication Data
US 2017/0143430 A1 May 25, 2017

Related U.S. Application Data

(60) Provisional application No. 62/259,513, filed on Nov. 24, 2015.

(51) Int. Cl.
*A61B 34/20* (2016.01)
*A61B 90/00* (2016.01)
(Continued)

(52) U.S. Cl.
CPC .............. *A61B 34/20* (2016.02); *A61B 5/055* (2013.01); *A61B 90/361* (2016.02); *A61B 90/39* (2016.02);
(Continued)

(58) Field of Classification Search
CPC ..... A61B 17/3403; A61B 34/10; A61B 34/20; A61B 2034/2046–2074; A61B 2034/107;
(Continued)

(56) References Cited

U.S. PATENT DOCUMENTS

| 7,072,705 B2 * | 7/2006 | Miga | G06K 9/00214 600/411 |
| 7,103,399 B2 * | 9/2006 | Miga | G06K 9/00214 600/411 |

(Continued)

OTHER PUBLICATIONS

Skrinjar O, Tagare H, Duncan J. Surface growing from stereo images. Computer Vision and Pattern Recognition, 2000 Proceedings IEEE Conference on 2000. p. 571-6 vol. 2.
(Continued)

*Primary Examiner* — Angela M Hoffa
(74) *Attorney, Agent, or Firm* — Locke Lord LLP; Tim Tingkang Xia, Esq.

(57) ABSTRACT

Methods and systems for performing trackerless image guided soft tissue surgery. For a patient in need of brain surgery, pre-operative preparation for a patient is performed by generating a three-dimensional textured point cloud (TPC) for the patient's scalp surface, and registering the first three-dimensional TPC to a magnetic resonance (MR) model of the brain. During the surgery, an intra-operative cortical surface registration to the MR model is performed for the MR-to-cortical surface alignment. Then shift measurement and compensation to the MR model is performed by: performing absolute deformation measurement of the brain based on the MR model with the cortical surface registration, and obtaining shift correction to the MR model using the absolute deformation measurements. The shift correction may be used for adjusting an image guidance system (IGS) in the brain surgery.

13 Claims, 16 Drawing Sheets
(14 of 16 Drawing Sheet(s) Filed in Color)

(51) Int. Cl.
    *A61B 34/10* (2016.01)
    *A61B 5/055* (2006.01)
    *G16H 50/50* (2018.01)
    *G01R 33/56* (2006.01)

(52) U.S. Cl.
    CPC ......... *G01R 33/5608* (2013.01); *G16H 50/50* (2018.01); *A61B 2034/107* (2016.02); *A61B 2034/2065* (2016.02); *A61B 2090/363* (2016.02); *A61B 2090/374* (2016.02); *A61B 2090/395* (2016.02); *A61B 2090/3983* (2016.02)

(58) Field of Classification Search
    CPC .............. A61B 90/37; A61B 2090/374; A61B 2090/395
    See application file for complete search history.

(56) References Cited

U.S. PATENT DOCUMENTS

| | | | | |
|---|---|---|---|---|
| 7,647,087 | B2 * | 1/2010 | Miga .................. | G06K 9/00214 600/411 |
| 8,195,272 | B2 * | 6/2012 | Piferi ............... | G01R 33/34007 128/845 |
| 8,315,689 | B2 * | 11/2012 | Jenkins ................. | A61B 34/25 600/410 |
| 8,644,906 | B2 * | 2/2014 | Piferi ............... | G01R 33/34007 600/410 |
| 8,957,812 | B1 * | 2/2015 | Hill ....................... | G01S 5/0027 342/445 |
| 9,314,305 | B2 * | 4/2016 | Jenkins ................ | A61B 5/7435 |
| 10,178,955 | B2 * | 1/2019 | Rucker ..................... | G06T 7/30 |
| 10,376,327 | B2 * | 8/2019 | Jenkins ................ | A61B 90/11 |
| 10,426,556 | B2 * | 10/2019 | Miga ..................... | A61B 8/085 |
| 2004/0019274 | A1 * | 1/2004 | Galloway, Jr. .......... | A61B 90/36 600/425 |
| 2005/0101855 | A1 * | 5/2005 | Miga .................. | G06K 9/00214 600/407 |
| 2006/0002630 | A1 * | 1/2006 | Fu ........................... | G06K 9/32 382/294 |
| 2008/0123927 | A1 * | 5/2008 | Miga ...................... | G06F 19/00 382/131 |
| 2011/0077504 | A1 * | 3/2011 | Fischer .................. | A61B 34/30 600/411 |
| 2011/0082383 | A1 * | 4/2011 | Cory ..................... | A61B 5/0536 600/547 |
| 2012/0330635 | A1 * | 12/2012 | Miga ......................... | G06T 7/33 703/11 |
| 2013/0063434 | A1 * | 3/2013 | Miga ...................... | G06F 19/00 345/420 |
| 2014/0037161 | A1 * | 2/2014 | Rucker ................. | A61B 5/0033 382/128 |
| 2014/0148808 | A1 * | 5/2014 | Inkpen ................... | G01B 7/003 606/80 |
| 2015/0142372 | A1 * | 5/2015 | Singh ................... | A61B 5/4851 702/150 |
| 2015/0157384 | A1 * | 6/2015 | Hoey ..................... | A61B 18/04 600/104 |
| 2016/0022146 | A1 * | 1/2016 | Piron ..................... | A61B 90/39 600/411 |
| 2016/0038252 | A1 * | 2/2016 | Barth, Jr. ............... | A61B 34/10 600/424 |
| 2017/0014203 | A1 * | 1/2017 | De Mathelin .......... | A61B 5/055 |
| 2017/0046833 | A1 * | 2/2017 | Lurie ...................... | G06T 19/20 |
| 2017/0112586 | A1 * | 4/2017 | Dhupar .................. | A61B 90/13 |

OTHER PUBLICATIONS

Clarkson MJ, Rueckert D, King AP, Edwards PJ, Hill DLG, Hawkes DJ. Registration of video images to tomographic images by optimising mutual information using texture mapping. Medical Image Computing and Computer-Assisted Intervention, Miccai'99, Proceedings1999. p. 579-89.

Edwards PJ, King AP, Maurer CR, de Cunha DA, Hawkes DJ, Hill DLG, et al. Design and evaluation of a system for microscope-assisted guided interventions (MAGI). Medical Image Computing and Computer-Assisted Intervention, Miccai'99, Proceedings1999. p. 842-852.

K. Sun, T. S. Pheiffer, A. L. Simpson, J. A. Weis, R. C. Thompson, and M. I. Miga, "Near real-time computer assisted surgery for brain shift correction using biomechanical models," IEEE Journal of Translational Engineering in Health and Medicine, vol. 2, 2014.

I. Chen, et . al, "Intraoperative brain shift compensation: Accounting for dural septa," IEEE Transactions on Biomedical Engineering, vol. 58, No. 3, pp. 499-508, 2011.

A. L. Simpson, T. S. Pheiffer, D. Caleb Rucker, A. K. Sills, K. Sun, R. C. Thompson, and M. I. Miga, 'Evaluation of conoscopic holography for estimating tumor resection cavities in model-based image-guided neurosurgery', IEEE Transactions on Biomedical Engineering, vol. 61, No. 6, pp. 1833-1843, 2014.

* cited by examiner

| # | Age [years] | Sex | Location of Tumor | Size [cm³] | # of points | Basis | Measured [mm] | Predicted [mm] | Error After Correction [mm] |
|---|---|---|---|---|---|---|---|---|---|
| 1 | 19 | F | RT | 4.8 | 52 | Wcp | 9.3 ± 1.4 (13.0) | 8.6 ± 0.3 (9.2) | 3.1 ± 1.4 (7.5) |
| 2 | 38 | F | LF | 1.3 | 13 | Wcp | 9.0 ± 1.6 (10.8) | 8.3 ± 1.2 (9.9) | 3.3 ± 1.2 (5.1) |
| 3 | 63 | F | LT | 25.1 | 18 | C | 12.8 ± 2.4 (17.7) | 12.1 ± 0.9 (13.0) | 4.0 ± 2.2 (8.2) |
| 4 | 51 | F | LT | 27.2 | 16 | C | 21.3 ± 3.5 (28.2) | 21.1 ± 3.2 (26.1) | 2.6 ± 1.1 (5.8) |
| 5 | 28 | F | RF | 7.6 | 11 | C | 11.2 ± 2.2 (14.7) | 10.6 ± 1.1 (12.1) | 3.3 ± 1.5 (5.2) |
| 6 | 63 | M | LF | 29.2 | 4 | C | 3.2 ± 0.9 (4.4) | 3.2 ± 0.4 (3.7) | 0.7 ± 0.4 (1.2) |
| 7 | 68 | F | LT | 16.1 | 213 | Wcp | 2.5 ± 1.0 (4.9) | 2.0 ± 0.2 (2.5) | 1.6 ± 0.8 (3.7) |
| 8 | 42 | F | RP | 100.2 | 20 | C | 7.1 ± 4.8 (22.3) | 6.1 ± 4.9 (25.3) | 2.5 ± 1.3 (6.7) |
| 9 | 64 | F | RF | 10.2 | 3 | C | 4.9 ± 0.2 (5.1) | 4.7 ± 0.7 (5.5) | 1.2 ± 0.4 (1.5) |
| 10 | 84 | F | LF | 47.3 | 13 | C | 6.8 ± 4.8 (17.0) | 6.5 ± 2.2 (10.4) | 3.3 ± 1.8 (7.5) |
| 11 | 48 | F | RT | 6.2 | 26 | C | 12.7 ± 2.8 (18.8) | 12.7 ± 0.9 (13.6) | 3.3 ± 1.3 (5.5) |
| 12 | 46 | M | RT | 56.8 | 17 | C | 15.0 ± 3.6 (22.1) | 13.2 ± 3.5 (17.4) | 3.7 ± 3.2 (13.6) |
| 13 | 22 | F | LF | 48.2 | 10 | C | 20.0 ± 4.3 (26.5) | 18.6 ± 2.9 (21.3) | 3.9 ± 2.5 (9.1) |
| 14 | 58 | M | LP | 23.1 | 12 | C | 6.3 ± 2.0 (10.3) | 5.7 ± 1.1 (7.3) | 1.9 ± 1.2 (4.3) |
| 15 | 77 | M | LT | 8.9 | 7 | C | 6.3 ± 0.5 (6.7) | 6.1 ± 0.1 (6.3) | 1.5 ± 0.7 (2.6) |
| 16 | 75 | F | LT | 21.8 | 22 | C | 13.0 ± 2.1 (15.9) | 10.3 ± 0.8 (11.3) | 3.7 ± 1.8 (6.9) |

FIG. 12A

METHOD AND SYSTEM FOR TRACKERLESS IMAGE GUIDED SOFT TISSUE SURGERY AND APPLICATIONS OF SAME

CROSS-REFERENCE TO RELATED PATENT APPLICATION

This application claims priority to and the benefit of, pursuant to 35 U.S.C. § 119(e), of U.S. provisional patent application Ser. No. 62/259,513, filed Nov. 24, 2015, entitled "METHOD AND SYSTEM FOR TRACKERLESS IMAGE GUIDED SOFT TISSUE SURGERY AND APPLICATIONS OF SAME," by Michael I. Miga, which is incorporated herein by reference in its entirety.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [4] represents the fourth reference cited in the reference list, namely, K. Sun, T. S. Pheiffer, A. L. Simpson, J. A. Weis, R. C. Thompson, and M. I. Miga, "Near real-time computer assisted surgery for brain shift correction using biomechanical models," *IEEE Journal of Translational Engineering in Health and Medicine*, Vol. 2, 2014.

STATEMENT AS TO RIGHTS UNDER FEDERALLY-SPONSORED RESEARCH

This invention was made with government support under Contract No. R01NS049251 awarded by the National Institutes of Health. The government has certain rights in the invention.

FIELD OF THE INVENTION

The present invention relates generally to image guided surgery technology, and more particularly to methods and systems for performing trackerless image guided soft tissue surgery, and applications thereof.

BACKGROUND OF THE INVENTION

The background description provided herein is for the purpose of generally presenting the context of the invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the invention.

The current state of the art for image guided surgical systems involves the use of optical and electromagnetic tracking technologies to localize tools as well as the physical patient in the operating field. Using these tools, geometric information of the physical patient is determined and corresponding equivalent information using digital tools is found within the diagnostic images of the patient. These two sets of information are aligned with a mathematical transformation and image guided surgery can take place. This is what is known as conventional image guided surgery. In order to use the focal point of a surgical microscope as a means to localize soft tissue, often times the surgical microscope itself is tracked with the same optical cameras used to track digitization tools. This combination of systems is quite cumbersome. Often it requires special coordination to ensure that all tools are seen by the camera as well as the scope.

Therefore, a heretofore unaddressed need exists in the art to address the aforementioned deficiencies and inadequacies.

SUMMARY OF THE INVENTION

One aspect of the present invention relates to a method for performing trackerless image guided soft tissue surgery on a living subject. In certain embodiments, the method includes: (a) performing pre-operative preparation for the living subject, including: generating a first three-dimensional textured point cloud (TPC) for a surface of the living subject covering an organ, wherein the organ is formed by the soft tissue; registering the first three-dimensional TPC to a magnetic resonance (MR) model of the organ; and performing an entry-into-body plan for the surface; (b) performing an intra-operative cortical surface registration to the MR model, including: opening the surface based on the entry-into-body plan to expose a cortical surface of the organ; generating a second three-dimensional TPC for the cortical surface; and performing a MR-to-cortical surface alignment by registering the second three-dimensional TPC to the MR model; and (c) performing shift measurement and compensation to the MR model of the organ, including: performing absolute deformation measurement of the organ based on the MR model with the cortical surface registration; obtaining shift correction to the MR model using the absolute deformation measurements; and adjusting an image guidance system (IGS) based on the shift correction for performing an operation to the organ.

In certain embodiments, the organ is a brain, the surface is a scalp surface of the living subject, and the entry-into-body plan is a craniotomy plan.

In certain embodiments, the step of generating the first three-dimensional TPC includes: placing a plurality of markings on the surface of the living subject; scanning at least one field of view (FOV) scanned image of the surface with the markings; and constructing the first three-dimensional TPC based on the at least one FOV scanned image. In certain embodiments, the step of scanning at least one FOV scanned image is performed by a stereo camera, a stereo-vision device, or a stereo-pair or laser scanning device. In certain embodiments, the markings are ink markings or geometrically distinct marking objects printed or adhered on the rigid surface of the living subject.

In certain embodiments, the step of performing an entry-into-body plan is conducted without a need of a separate optical tracking device.

In certain embodiments, the step (a) further includes: performing segmentation and building the MR model; and constructing a pre-operative atlas.

In certain embodiments, the method further includes: (d) performing an intra-operative post-resection registration to the MR model; and (e) performing shift measurement and compensation to the MR model with the post-resection registration.

Another aspect of the present invention relates to a method for performing trackerless image guided soft tissue surgery on a living subject. In certain embodiments, the method includes: (a) performing at least one image-to-physical registration to the living subject; (b) performing absolute deformation measurement of an organ of the living subject based on the at least one image-to-physical registration, wherein the organ is formed by the soft tissue; (c) performing shift correction to the organ using the absolute deformation measurements; and (d) adjusting an image guidance system (IGS) based on the shift correction for performing operation to the organ.

In certain embodiments, the step (a) includes: (1) performing a pre-operative registration to the organ by: generating a first three-dimensional textured point cloud (TPC) for a surface of the living subject covering the organ; and registering the first three-dimensional TPC to a magnetic resonance (MR) model of the organ; and (2) performing an intra-operative cortical surface registration to the MR model for a MR-to-cortical surface alignment. In certain embodiments, the step (a) further includes: (3) performing an intra-operative post-resection registration to the MR model.

In certain embodiments, the step (1) further includes: performing segmentation and building the MR model; and constructing a pre-operative atlas.

In certain embodiments, the step of generating a first three-dimensional TPC includes: placing a plurality of markings on a surface of the living subject; scanning at least one field of view (FOV) scanned image of the surface with the markings; and constructing the three-dimensional TPC based on the at least one FOV scanned image. In certain embodiments, the step of scanning at least one FOV scanned image is performed by a stereo camera, a stereovision device, or a stereo-pair or laser scanning device. In certain embodiments, the markings are ink markings or geometrically distinct marking objects printed or adhered on the surface of the living subject.

In certain embodiments, the organ is a brain, and the surface is a scalp surface of the living subject.

In certain embodiments, the step (1) further comprises: performing a craniotomy plan for the surface without need of a separate optical tracking device.

In certain embodiments, the step (2) includes: opening the surface based on the craniotomy plan to expose a cortical surface of the organ; generating a second three-dimensional TPC for the cortical surface; and performing the MR-to-cortical surface alignment by registering the second three-dimensional TPC to the MR model.

Certain aspects of the present invention relate to a system for performing trackerless image guided soft tissue surgery, which includes an image guidance framework configured to perform the method as described above.

These and other aspects of the invention will become apparent from the following description of the preferred embodiment taken in conjunction with the following drawings, although variations and modifications therein may be affected without departing from the spirit and scope of the novel concepts of the invention.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

The accompanying drawings illustrate one or more embodiments of the invention and, together with the written description, serve to explain the principles of the invention. Wherever possible, the same reference numbers are used throughout the drawings to refer to the same or like elements of an embodiment.

FIG. 12A shows a chart of quantitative surface comparison of 16 patients according to certain embodiments of the present invention.

DETAILED DESCRIPTION OF THE INVENTION

Figure 1:
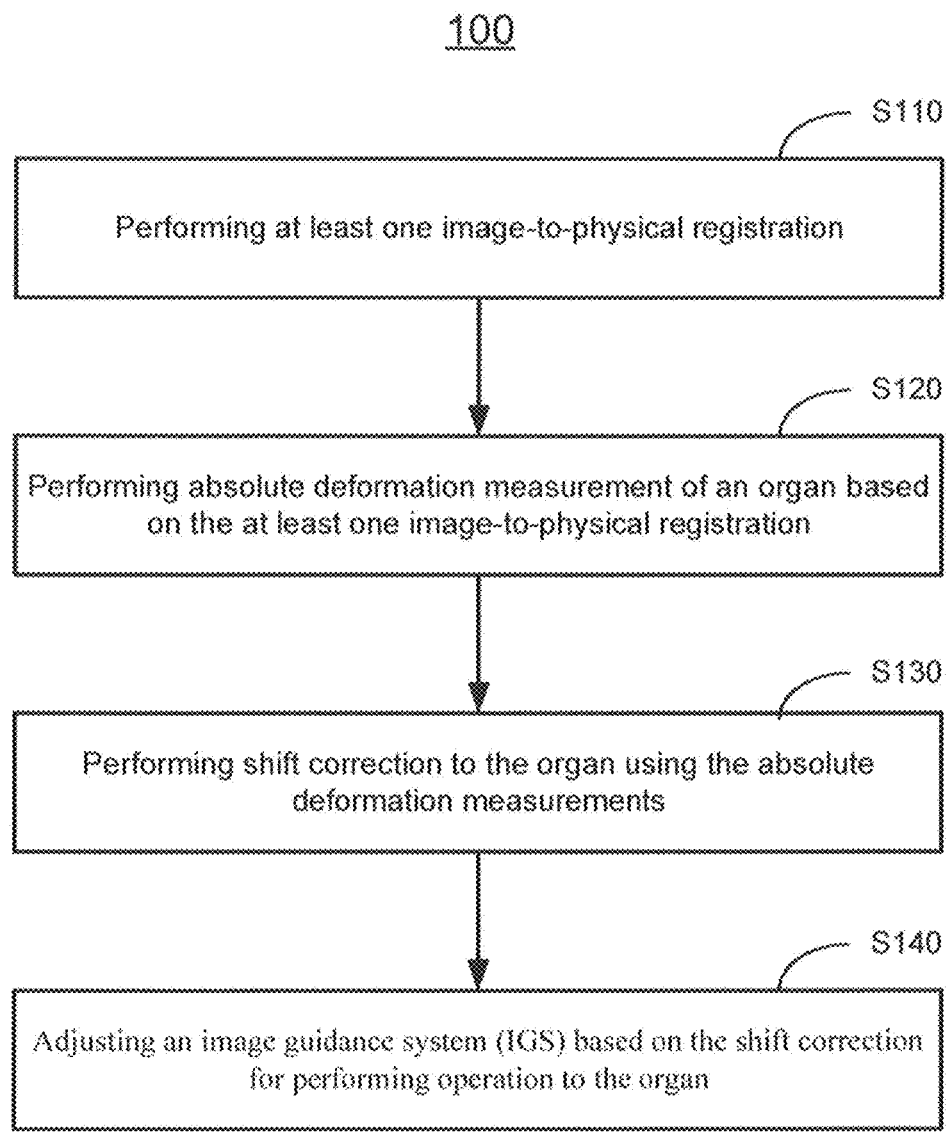
FIG. 1 shows a flowchart of a method for performing trackerless image guided soft tissue surgery on a living subject according to certain embodiments of the present invention.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that, as used in the description herein and throughout the claims that follow, the meaning of "a", "an", and "the" includes plural reference unless the context clearly dictates otherwise. Also, it will be understood that when an element is referred to as being "on" another element, it can be directly on the other element or intervening elements may be present there between. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

It will be further understood that the terms "comprises" and/or "comprising," or "includes" and/or "including" or "has" and/or "having", or "carry" and/or "carrying," or "contain" and/or "containing," or "involve" and/or "involving, and the like are to be open-ended, i.e., to mean including but not limited to. When used in this disclosure, they specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about", "substantially" or "approximately" shall generally mean within 20 percent, preferably within 10 percent, and more preferably within 5 percent of a given value or range. Numerical quantities given herein are approximate, meaning that the term "around", "about", "substantially" or "approximately" can be inferred if not expressly stated.

As used herein, the phrase "at least one of A, B, and C" should be construed to mean a logical (A or B or C), using a non-exclusive logical OR. It should be understood that one or more operations within a method is executed in different order (or concurrently) without altering the principles of the invention.

Embodiments of the invention are illustrated in detail hereinafter with reference to accompanying drawings. It should be understood that specific embodiments described herein are merely intended to explain the invention, but not intended to limit the invention. In accordance with the purposes of this invention, as embodied and broadly described herein, this invention, in certain aspects, relates to methods and systems for performing trackerless image guided soft tissue surgery, and applications thereof.

To address the aforementioned deficiencies and inadequacies in the conventional image guided surgery, certain aspects of the invention relate to an approach where the conventional guidance is no longer needed but rather all surgical guidance can be conducted through the surgical microscope environment. This includes image-to-physical registration, measurements of brain deformations, correction for deformations, and successful image guidance through the surgical environment. To the inventor's knowledge, there are no existing trackerless surgical microscope systems that can perform image-to-physical registration and deformation correction, and there are no existing solution proposed that was devoid of optical tracking technologies.

In certain aspects, the invention relates to a novel system design for a trackerless surgical microscope image guided system. Current image guided surgery technology involves the integration of the surgical microscope and a separate image guided surgery system. Typically, the surgical microscope is optically tracked using a tracked target attached to the scope. A separate optical camera tracking system (associated with the conventional image guided system) is used to then track the scope as well as other surgical instrumentation. In our new design, the conventional image guided system is no longer needed and the entire guidance environment can be realized within the microscope environment.

One aspect of the present invention relates to a method for performing trackerless image guided soft tissue surgery on a living subject. In certain embodiments, the method includes: (a) performing pre-operative preparation for the living subject, including: generating a first three-dimensional textured point cloud (TPC) for a surface of the living subject covering an organ, wherein the organ is formed by the soft tissue; registering the first three-dimensional TPC to a magnetic resonance (MR) model of the organ; and performing an entry-into-body plan for the surface; (b) performing an intra-operative cortical surface registration to the MR model, including: opening the surface based on the entry-into-body plan to expose a cortical surface of the organ; generating a second three-dimensional TPC for the cortical surface; and performing a MR-to-cortical surface alignment by registering the second three-dimensional TPC to the MR model; and (c) performing shift measurement and compensation to the MR model of the organ, including: performing absolute deformation measurement of the organ based on the MR model with the cortical surface registration; obtaining shift correction to the MR model using the absolute deformation measurements; and adjusting an image guidance system (IGS) based on the shift correction for performing an operation to the organ.

Another aspect of the present invention relates to a method for performing trackerless image guided soft tissue surgery on a living subject. In certain embodiments, the method includes: (a) performing at least one image-to-physical registration to the living subject; (b) performing absolute deformation measurement of an organ of the living subject based on the at least one image-to-physical registration, wherein the organ is formed by the soft tissue; (c) performing shift correction to the organ using the absolute deformation measurements; and (d) adjusting an image guidance system (IGS) based on the shift correction for performing operation to the organ.

Certain aspects of the present invention relate to a system for performing trackerless image guided soft tissue surgery, which includes an image guidance framework configured to perform the method as described above.

These and other aspects of the present invention are further described below.

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

FIG. 1 shows a flowchart of a method for performing trackerless image guided soft tissue surgery on a living subject according to certain embodiments of the present invention. It should be particularly noted that, unless otherwise stated in the present disclosure, the steps of the method may be arranged in a different sequential order, and are thus not limited to the sequential order as shown in FIG. 1.

As shown in FIG. 1, in step S110, at least one image-to-physical registration is performed to the living subject, i.e., a patient for the surgery. Then, in step S120, absolute deformation measurement of an organ may be performed based on the at least one image-to-physical registration. In step S130, shift correction to the organ is performed using the absolute deformation measurements. Once the shift correction is performed, in step S140, the shift correction may be used for adjusting an image guidance system (IGS) based on the shift correction for performing operation to the organ.

In certain embodiments, the image-to-physical registration in step S110 may include multiple registrations. For example, for a patient having a brain surgery, the image-to-physical registration may include a pre-operative registration, an intra-operative cortical surface registration, and an intra-operative post-resection registration.

In certain embodiments, the pre-operative registration to the organ (i.e., the brain) is a part of the pre-operative preparation process, which may include: generating a first three-dimensional textured point cloud (TPC) for a surface (i.e., the scalp surface) of the living subject covering the organ; registering the first three-dimensional TPC to a magnetic resonance (MR) model of the organ; and performing an entry-into-body plan for the surface. In certain embodiments, when the organ is the brain, the entry-into-body plan may be a craniotomy plan.

In certain embodiments, the step of generating a first three-dimensional TPC includes: placing a plurality of markings on a surface of the living subject; scanning at least one field of view (FOV) scanned image of the surface with the markings; and constructing the three-dimensional TPC based on the at least one FOV scanned image.

Figure 2:
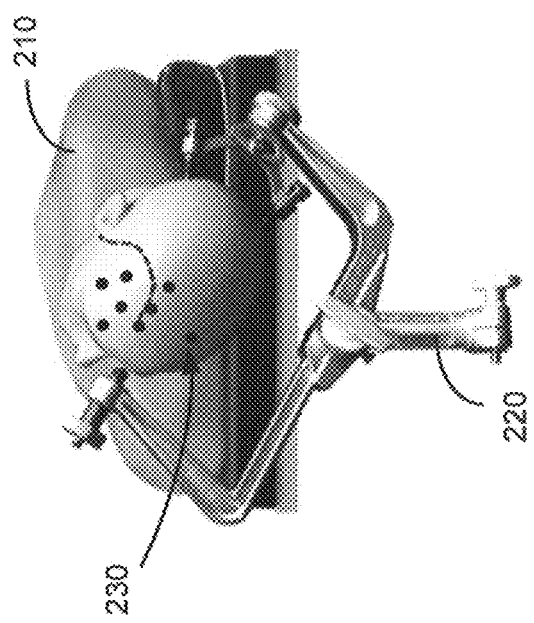
FIG. 2 schematically shows a plot of placing ink markings on the scalp of a patient according to certain embodiments of the present invention.

FIG. 2 schematically shows a plot of placing ink markings on the scalp of a patient according to certain embodiments of the present invention. In most surgical settings, it is common for a surgeon to use markings and sketched out contours on the patient to plan procedures. As shown in FIG. 2, a patient 210 is in a Mayfield clamp 220, and ink markings 230 have been placed on the patient's scalp surface. In certain embodiments, for the purposes of the trackerless system, ink markings may be printed on the scalp surface, or perhaps adhered. In certain embodiments, it would also be possible to use geometrically distinct objects as the markings to be adhered on the scalp surface.

Figure 3:
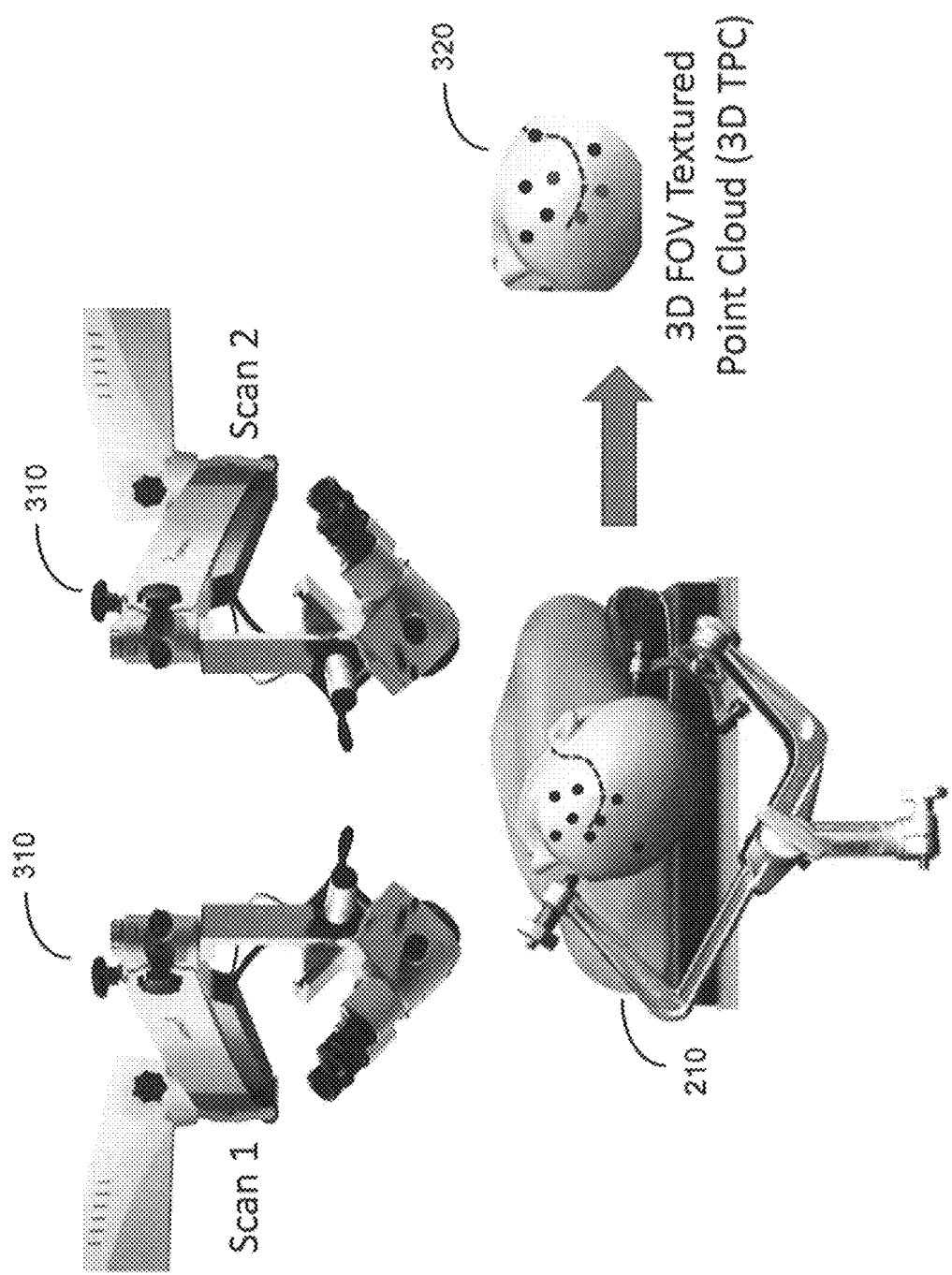
FIG. 3 schematically shows a plot of scanning FOV scanned images and constructing the three-dimensional TPC according to certain embodiments of the present invention.

FIG. 3 schematically shows a plot of scanning FOV scanned images and constructing the three-dimensional TPC according to certain embodiments of the present invention. As shown in FIG. 3, one or more stereo-pair or laser scanning devices 310 may be used for scanning the patient with markings. In certain embodiments, the step of scanning the images may be performed by a stereo camera, a stereo-vision device, a stereo-pair or laser scanning device, or any other similar image capturing devices. Once the scanned images are obtained, using principles of computer vision, a 3D colored textured point cloud (TPC) 320, which may be colored with the digital image of the patient in the field of view (FOV), may be constructed. In certain embodiments, more than one scan may be conducted from different vantage points to construct a more complete surface. The only requirement is that sufficient common structures in scans be available for alignment purposes. For example, in the 3D TPC 320, if the dots could be seen in both Scan 1 and Scan 2, the 3D TPC could be aligned with each other and appended to generate a more complete 3D TPC. It should be particularly noted that none of the above process requires tracking the scope with another digitization technology.

Figure 4:
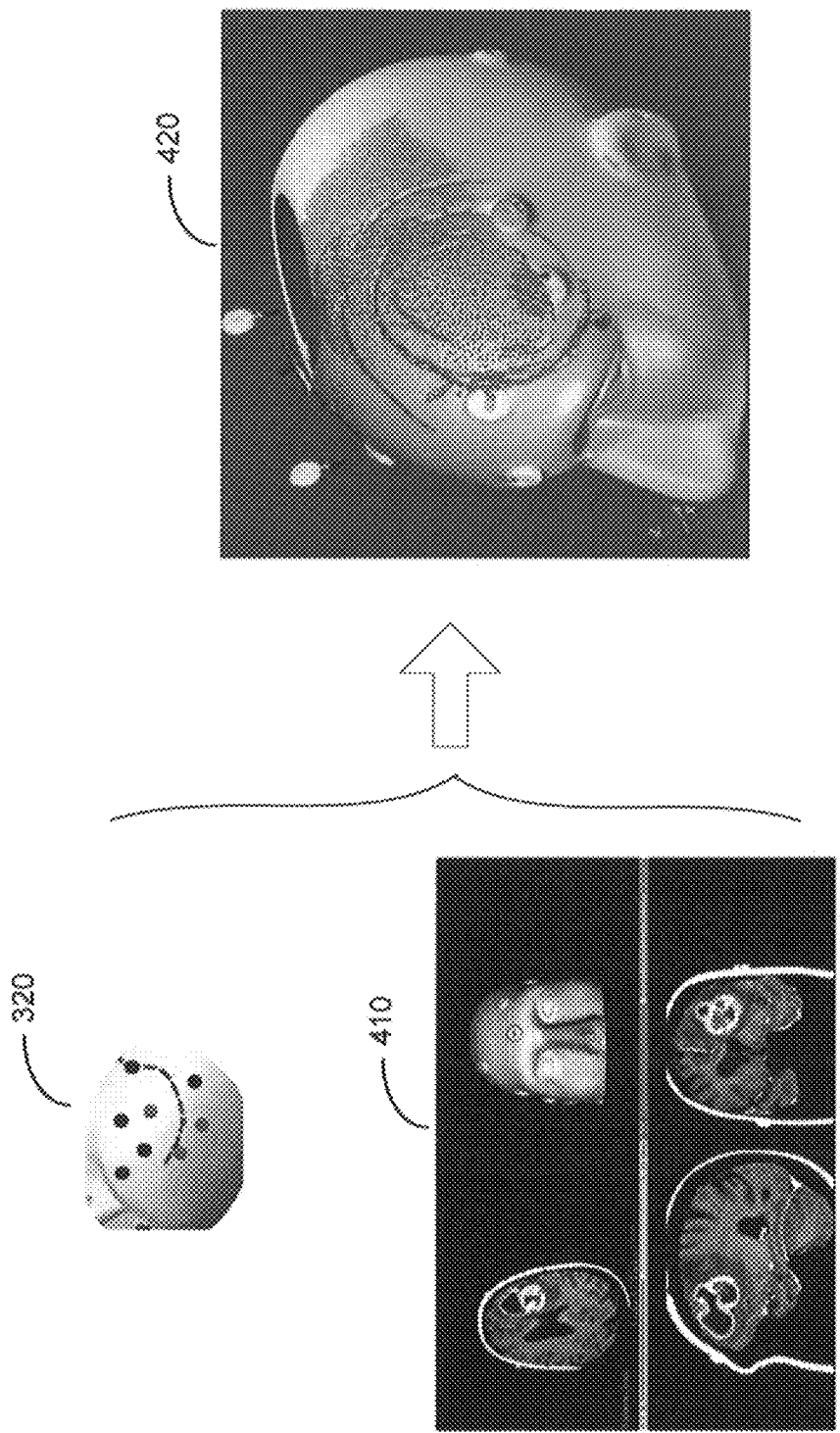
FIG. 4 schematically shows a plot of the pre-operative organ-to-MR registration according to certain embodiments of the present invention.

Once the first three-dimensional TPC 320 is obtained, registration of the first three-dimensional TPC to a magnetic resonance (MR) model of the organ may be conducted. FIG. 4 schematically shows a plot of the pre-operative organ-to-MR registration according to certain embodiments of the present invention. As shown in FIG. 4, the 3D TPC 320 and the MR model 410 (or MR equivalent surface) can be registered using surface-based techniques, e.g., iterative closest point, in order to generate a fused 3D TPC-to-MR display 420. In certain embodiments, because a textured cloud with markings is used, any preoperative planning regarding approach to the tumor based on the imaging data and established with respect to the scalp surface in the MR model can be fused with 3D TPC visible field and used for planning. As a result, conventional planning can still happen but without need of tracking technology. However, the conventional planning would no longer be necessary. Rather, a fused 3D TPC-to-MR display 420 as shown in FIG. 4 would be provided as the initial MR-to-patient alignment.

Figure 5:
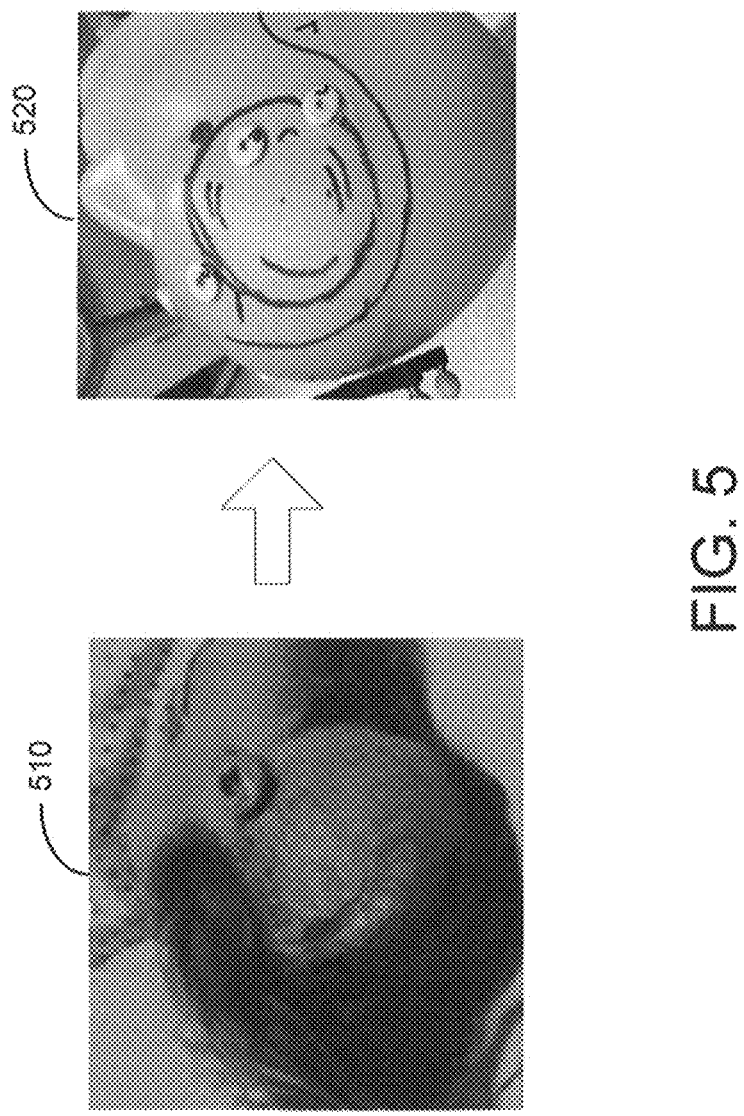
FIG. 5 schematically shows a plot of craniotomy plan after registration according to certain embodiments of the present invention.

After the TPC-to-MR registration, an entry-into-body plan on the patient's surface, such as a craniotomy plan on the patient's scalp surface, may be conducted. FIG. 5 schematically shows a plot of craniotomy plan after registration according to certain embodiments of the present invention. As shown in FIG. 5, a fused 3D TPC-to-MR display 510 may be used to perform the craniotomy plan 520. In certain embodiments, the craniotomy plan 520 may be performed with a connect-the-dots approach in the visible FOV display 510. It should be noted that the craniotomy plan process can also be performed without need of a separate optical tracking technology. In certain embodiments, the only thing needed is a nice display with optimal fused image capabilities. Further, in certain embodiments, when the surgery is perform not to the brain of the patient but to another organ of the patient which is not the brain, the entry-into-body plan may not be a craniotomy plan.

Figure 6:
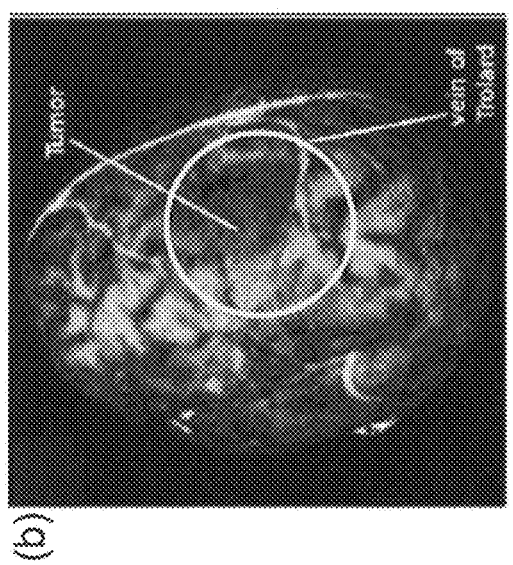
FIG. 6 schematically shows a plot of the intra-operative cortical surface registration according to certain embodiments of the present invention, where (a) shows the MR model with the pre-operative organ-to-MR registration; (b) shows a cortical surface of the MR model; (c) shows the cortical surface after craniotomy; and (d) shows the MR model for the cortical registration.
Figure 6:
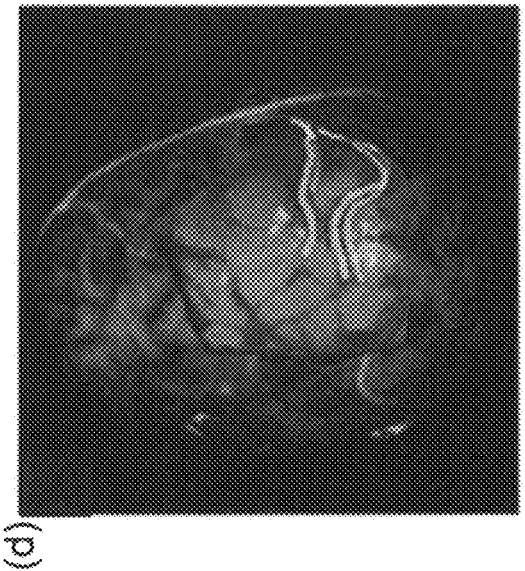
Figure 6:
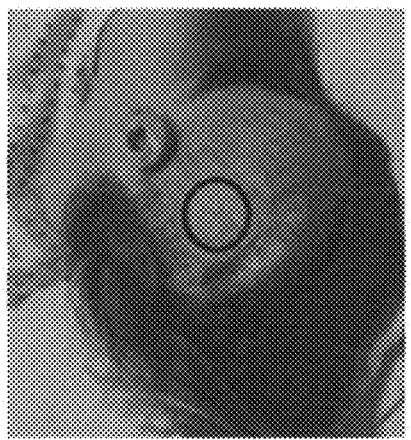
Figure 6:
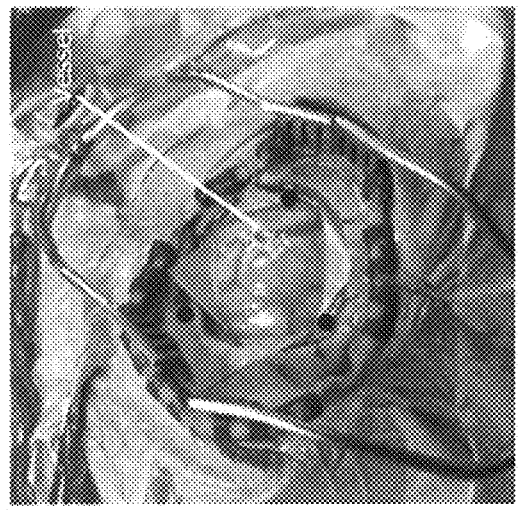

Once the pre-operative preparation for the patient is complete, the surgery may be conducted, beginning with an intra-operative cortical surface registration to the MR model. FIG. 6 schematically shows a plot of the intra-operative cortical surface registration according to certain embodiments of the present invention, where (a) shows the MR model with the pre-operative organ-to-MR registration; (b) shows a cortical surface of the MR model; (c) shows the cortical surface after craniotomy; and (d) shows the MR model for the cortical registration. In certain embodiments, with the initial MR-to-patient alignment provided in the pre-operative preparation process, as shown in FIG. 6(a), the craniotomy approximation will provide the approximate corresponding MR surface, as shown as a circle in FIG. 6(b), which will be visible upon opening the dura. Specifically, FIG. 6(b) shows the tumor area and the vein of trolard. Then the microscope can be used again to capture the visible cortical surface creating a second 3D TPC, as shown in FIG. 6(c). It should be noted that, at this time, visible markings will be adhered to the rigid bone surface (implants or soft-designated-black dots) as shown in FIG. 6(c). In certain embodiments, the markings may also be unique geometric reference targets. With each subsequent scan of the microscope, these markings can be used to realign the fields of view in reference to each other. This will allow absolute measurements relative to the bone. Once the cortical surface is acquired, MR-to-Cortical surface alignment can then be done, as shown in FIG. 6(d).

Figure 7:
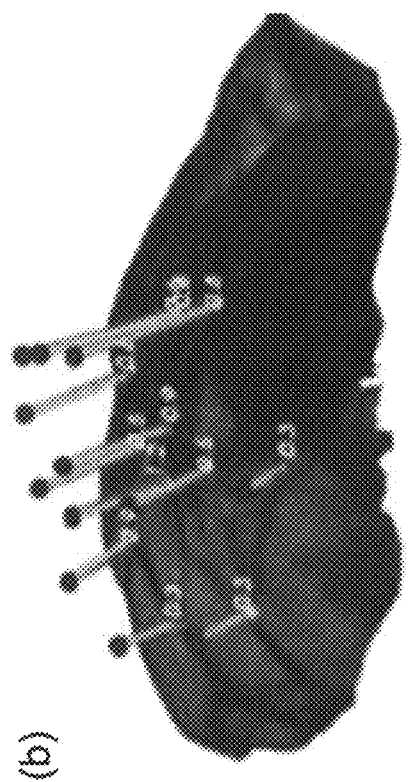
FIG. 7 schematically shows a plot of the absolute deformation measurement of an organ according to certain embodiments of the present invention, where (a) shows the cortical surface after craniotomy, and (b) shows the MR model labeling the absolute deformation measurements.
Figure 7:
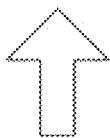
Figure 7:
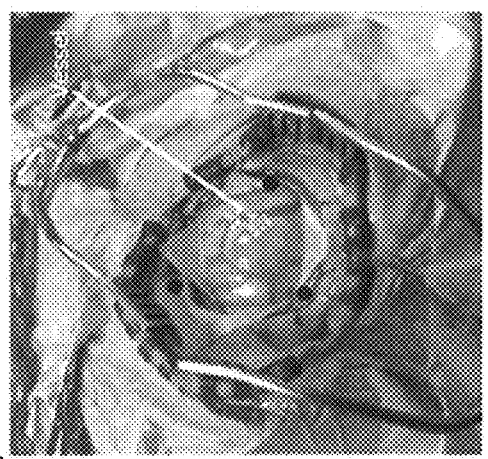

Once the cortical registration is complete, absolute deformation measurement of an organ may be performed based on the MR model after the cortical registration. FIG. 7 schematically shows a plot of the absolute deformation measurement of an organ according to certain embodiments of the present invention, where (a) shows the cortical surface after craniotomy, and (b) shows the MR model labeling the absolute deformation measurements. As described above, markings (such as the black dots) or reference target as shown in FIG. 7(a) may be used to continuously re-register during case. All deformation shifts are relative to this coordinate system. Because all 3D TPCs obtained during the surgery may be related to the reference target, the 3D absolute deformation measurements of brain shift may be obtained, as shown in FIG. 7(b). Once the absolute deformation measurements are obtained, shift correction to the organ (i.e., the brain) can be performed using the absolute deformation measurements. Then the shift correction may be used for adjusting an image guidance system (IGS) based on the shift correction for performing operation to the organ.

In certain embodiments, a correction scheme could be driven by these measurements. It should be noted that the correction scheme may be applied to any correction system available, without the need of using a separate optical tracking system.

Figure 8:
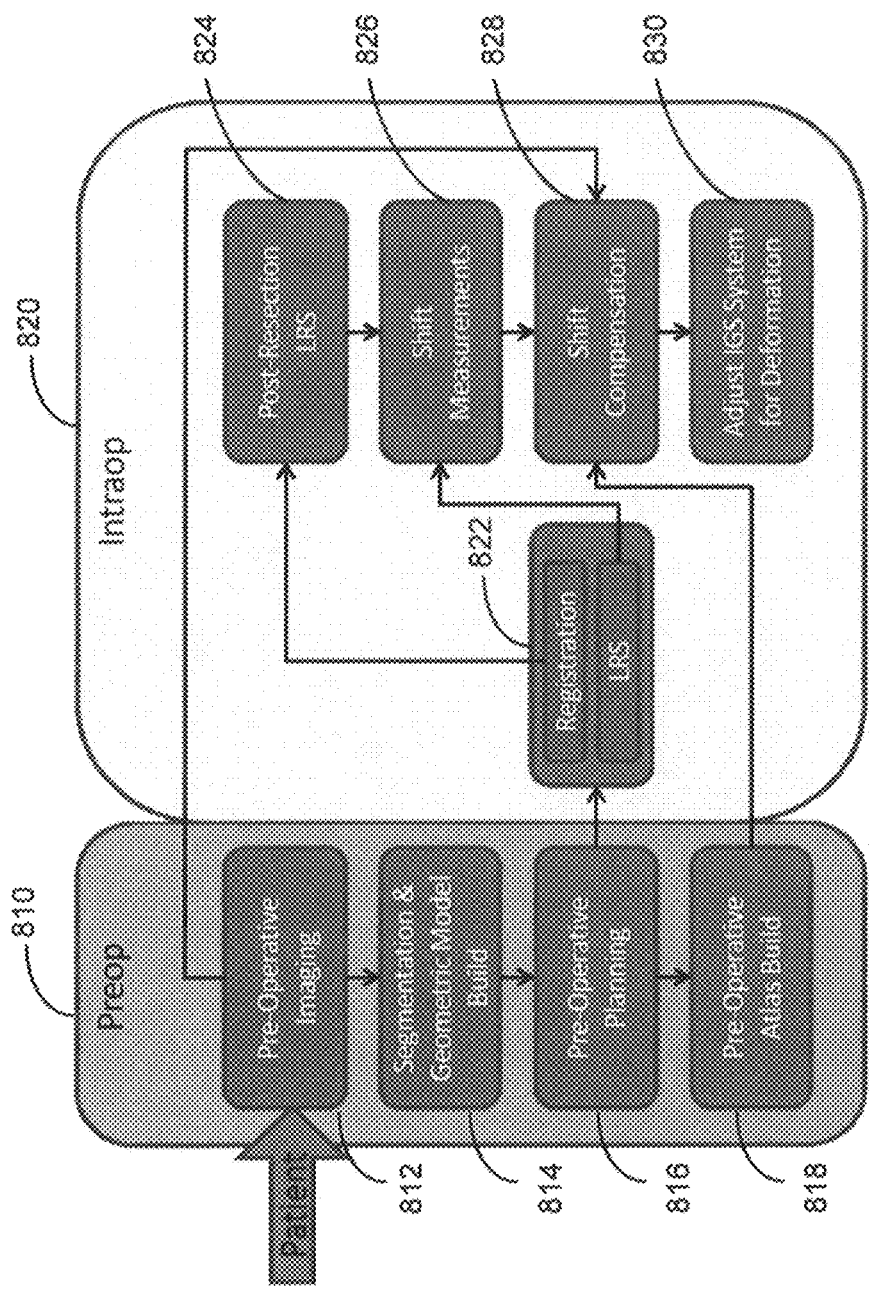
FIG. 8 schematically shows a block diagram of a process for performing trackerless image guided soft tissue surgery on a living subject according to certain embodiments of the present invention.
Figure 9B:
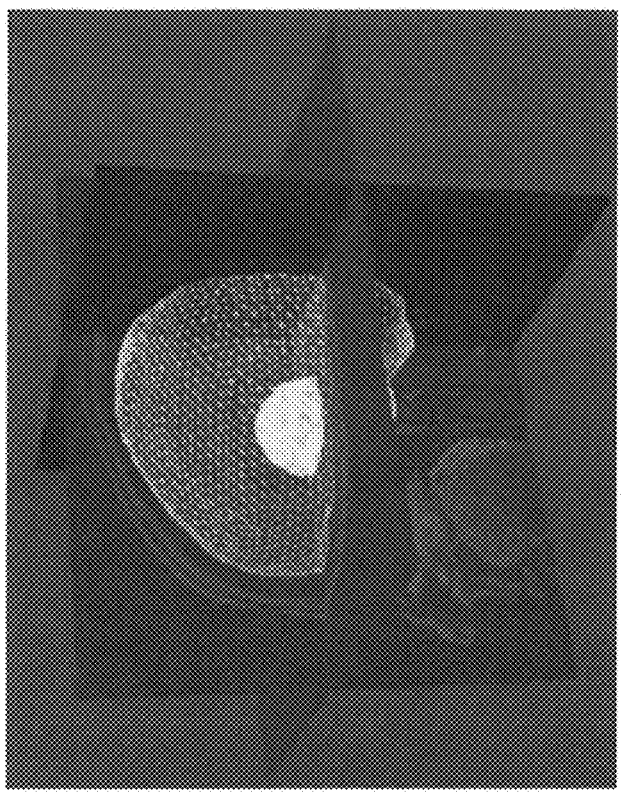
FIG. 9B schematically shows an example of segmentation and geometric model building as shown in the process of FIG. 8 according to certain embodiments of the present invention.
Figure 9A:
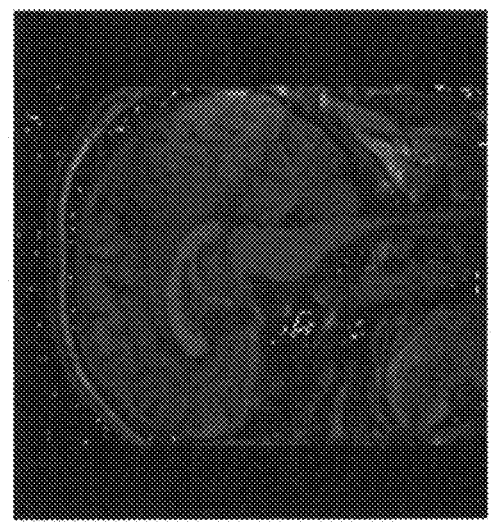
FIG. 9A schematically shows an example of pre-operative imaging as shown in the process of FIG. 8 according to certain embodiments of the present invention.
Figure 9D:
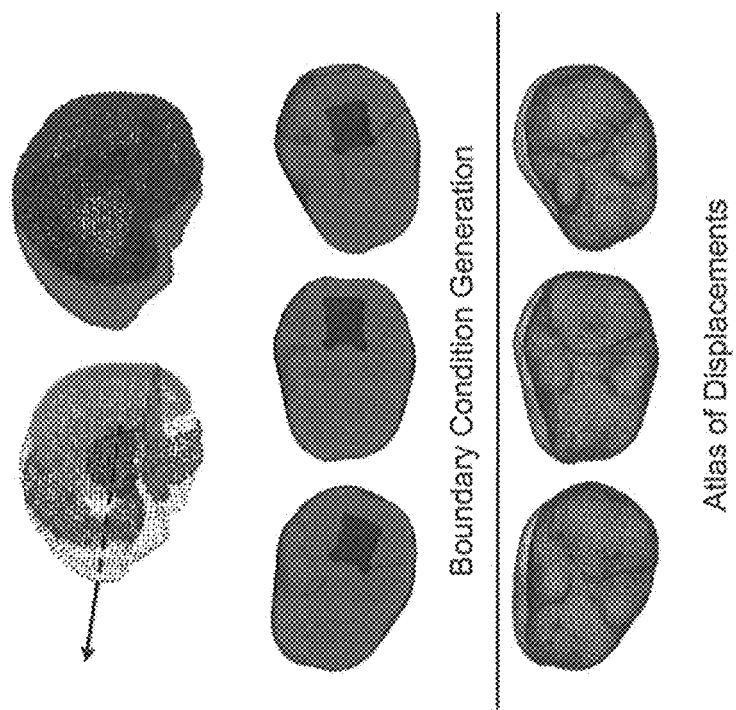
FIG. 9D schematically shows an example of pre-operative atlas build as shown in the process of FIG. 8 according to certain embodiments of the present invention.
Figure 9C:
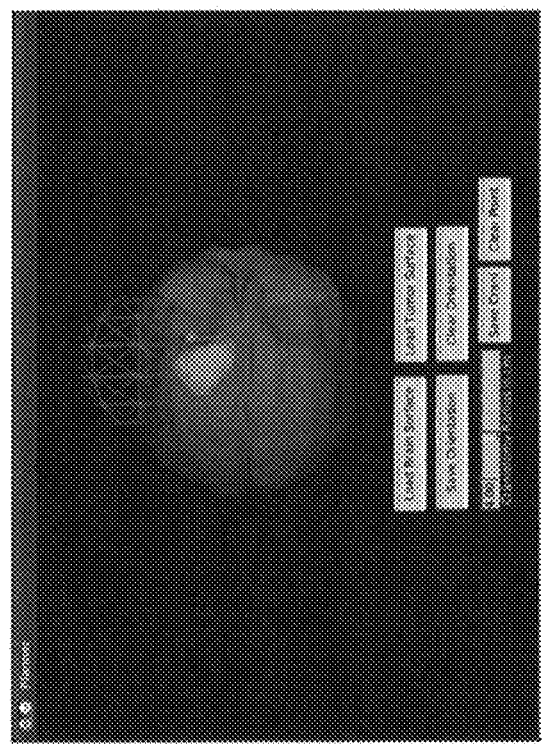
FIG. 9C schematically shows an example of pre-operative planning as shown in the process of FIG. 8 according to certain embodiments of the present invention.

FIG. 8 schematically shows a block diagram of a process for performing trackerless image guided soft tissue surgery on a living subject according to certain embodiments of the present invention. As shown in FIG. 8, the process has two stages, including a pre-operative stage 810 and an intra-operative stage 820. The pre-operative stage 810 includes pre-operative imaging 812, segmentation and geometric model building 814, pre-operative planning 816, and pre-operative atlas build 818. The intra-operative stage 820 includes an intra-operative registration with LRS 822, a post-resection LRS 824, shift measurements 826, shift compensation 828, and the process to adjust the IGS system for deformation 830. It should be noted that the process is provided as one embodiment, and unless otherwise stated in the present disclosure, the steps of the process may be arranged in a different sequential order, and are thus not limited to the sequential order as shown in FIG. 8.

In certain embodiments, with intra-operative MR, the cost is an issue. Alternatively, sparse imaging modalities like stereoscopic microscope or LRS may be used. The LRS system is tracked in physical space, which acquires the surface points and textured images, and then combines them to give textured surfaces. Thus, the LRS can get serial scans in the OR, before and after resection to obtain a measurement of shift.

FIGS. 9A to 9D schematically shows examples of pre-operative imaging 812, segmentation and geometric model building 814, pre-operative planning 816 and pre-operative atlas build 818 as shown in the process of FIG. 8 according to certain embodiments of the present invention. In certain embodiments, atlas generation in the pre-operative atlas build process 818 involves computation of 720 model solutions as follows:

[Gravity—360 solutions] 3 fluid drainage levels, 60 head orientations, (×2) with and without resection;
[Mannitol—360 solutions] 3 capillary permiablilities, 60 head orientations, (×2) with and without resection.

Figure 10B:
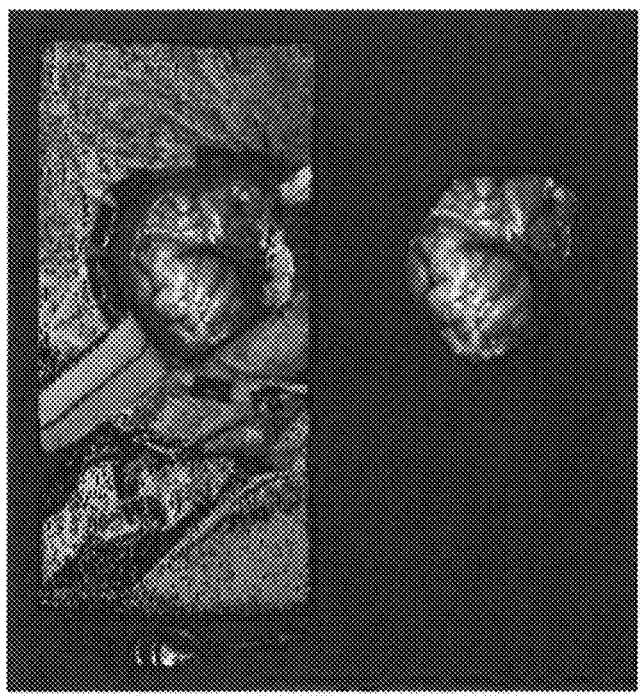
FIG. 10B schematically shows an example of post-resection LRS as shown in the process of FIG. 8 according to certain embodiments of the present invention.
Figure 10A:
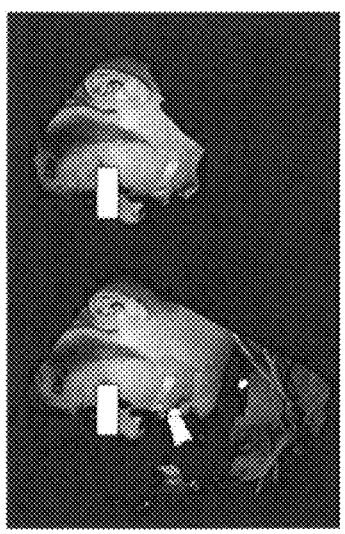
FIG. 10A schematically shows an example of intra-operative registration with LRS as shown in the process of FIG. 8 according to certain embodiments of the present invention.
Figure 10A:
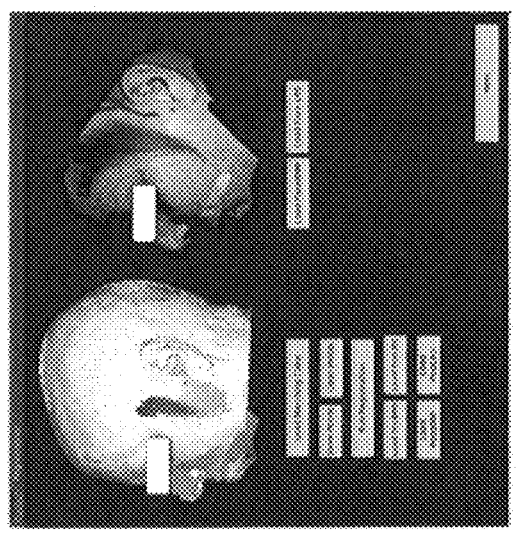
Figure 10C:
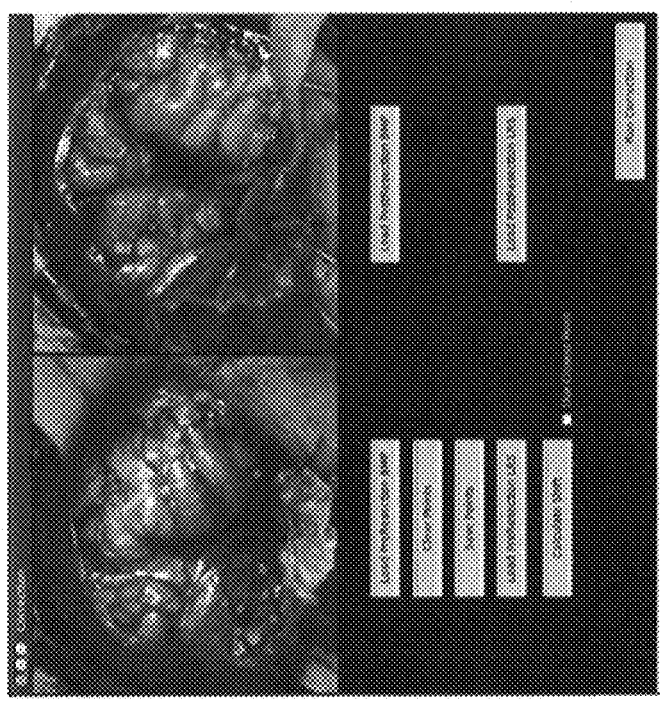
FIG. 10C schematically shows an example of shift measurements and shift compensation as shown in the process of FIG. 8 according to certain embodiments of the present invention.

FIG. 10A schematically shows an example of intra-operative registration with LRS as shown in the process of FIG. 8 according to certain embodiments of the present invention. FIG. 10B schematically shows an example of post-resection LRS as shown in the process of FIG. 8 according to certain embodiments of the present invention. FIG. 10C schematically shows an example of shift measurements and shift compensation as shown in the process of FIG. 8 according to certain embodiments of the present invention. In certain embodiments, resection simulated by decoupling nodes assigned as tumor via manual segmentation.

Figure 11:
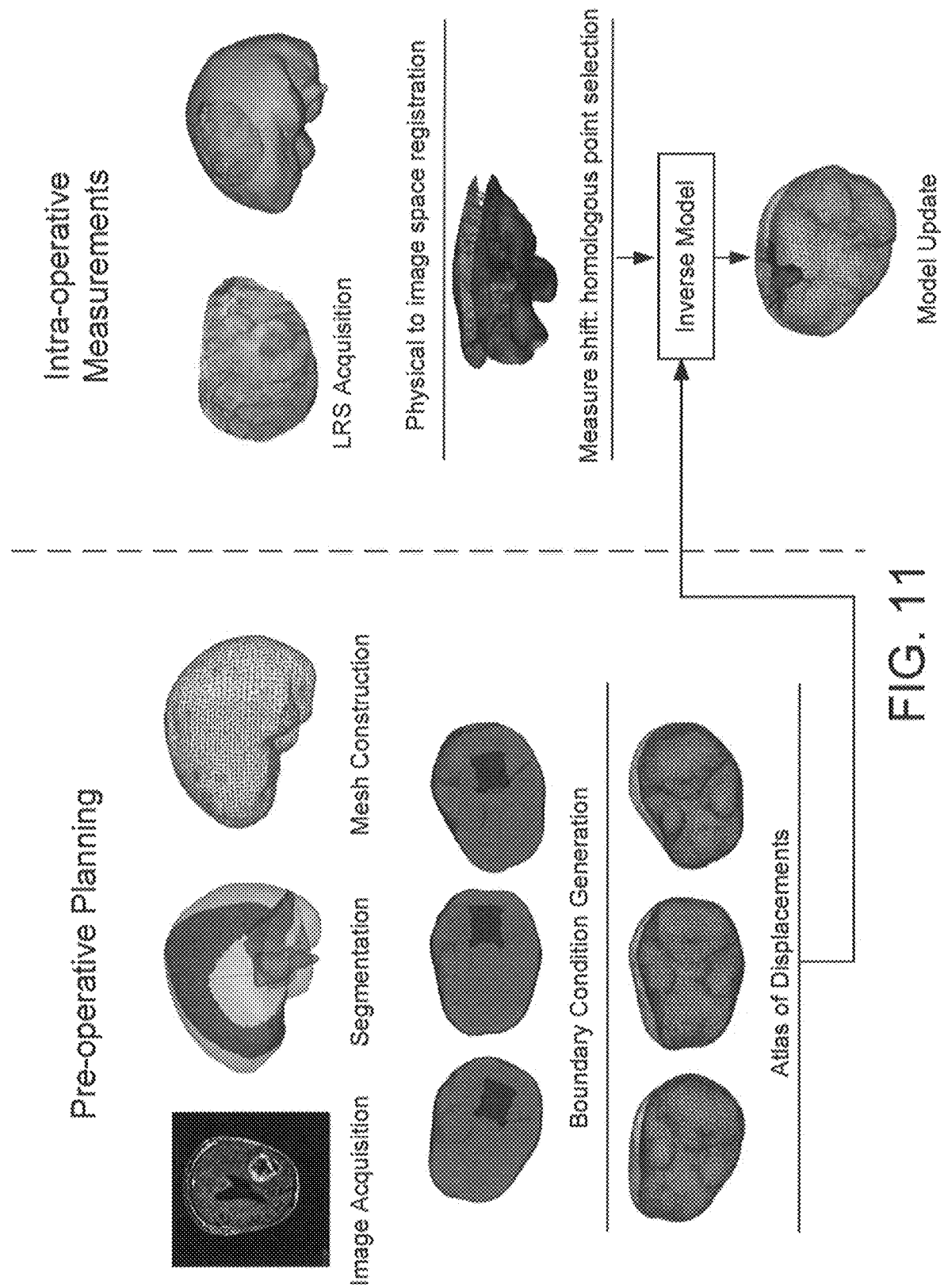
FIG. 11 schematically shows a plot of a process for performing trackerless image guided soft tissue surgery on a living subject according to certain embodiments of the present invention.

FIG. 11 schematically shows a plot of a process for performing trackerless image guided soft tissue surgery on a living subject according to certain embodiments of the present invention. As shown in FIG. 11, the process includes generally all of the steps as shown in FIG. 8.

In order to show that the methods and processes proposed may be used for performing trackerless image guided soft tissue surgery on a living subject, the inventor has conducted the following experiment as described below.

EXPERIMENT

Certain embodiments of the method are tested on 16 patients. In particular, certain embodiments of the invention may be used in the development of a system that allows image-guidance without the use of separate tracking technologies. In certain embodiments, soft-tissue cortical surface deformation measurements may be conducted without the use of separate tracking technologies. In other words, by adopting the methods and processes proposed in the above-mentioned embodiments, brain surface deformations may be measured.

FIG. 12A shows a chart of quantitative surface comparison of 16 patients according to certain embodiments of the present invention. Specifically, as shown in FIG. 12A, the quantitative surface comparison table of the 16 patients include three columns, respectively labeled as 'Measured,' 'Predicted' and 'Error After Correction.' The column labeled 'Measured' reflects the amount of average brain surface displacement that occurred during the surgery as a result from measuring cortical surface displacements from 3D textured point clouds. The 'Predicted' column represents the embodiment of a correction strategy. The last column labeled 'Error After Correction' is the remaining error in localization after correction. It should be noted that the data as shown in FIG. 12A is obtained without the need of separate tracking technologies, and the displacements were measured by analyzing textured point cloud data changes which can be acquired by the trackerless method as described above.

Figure 12B:
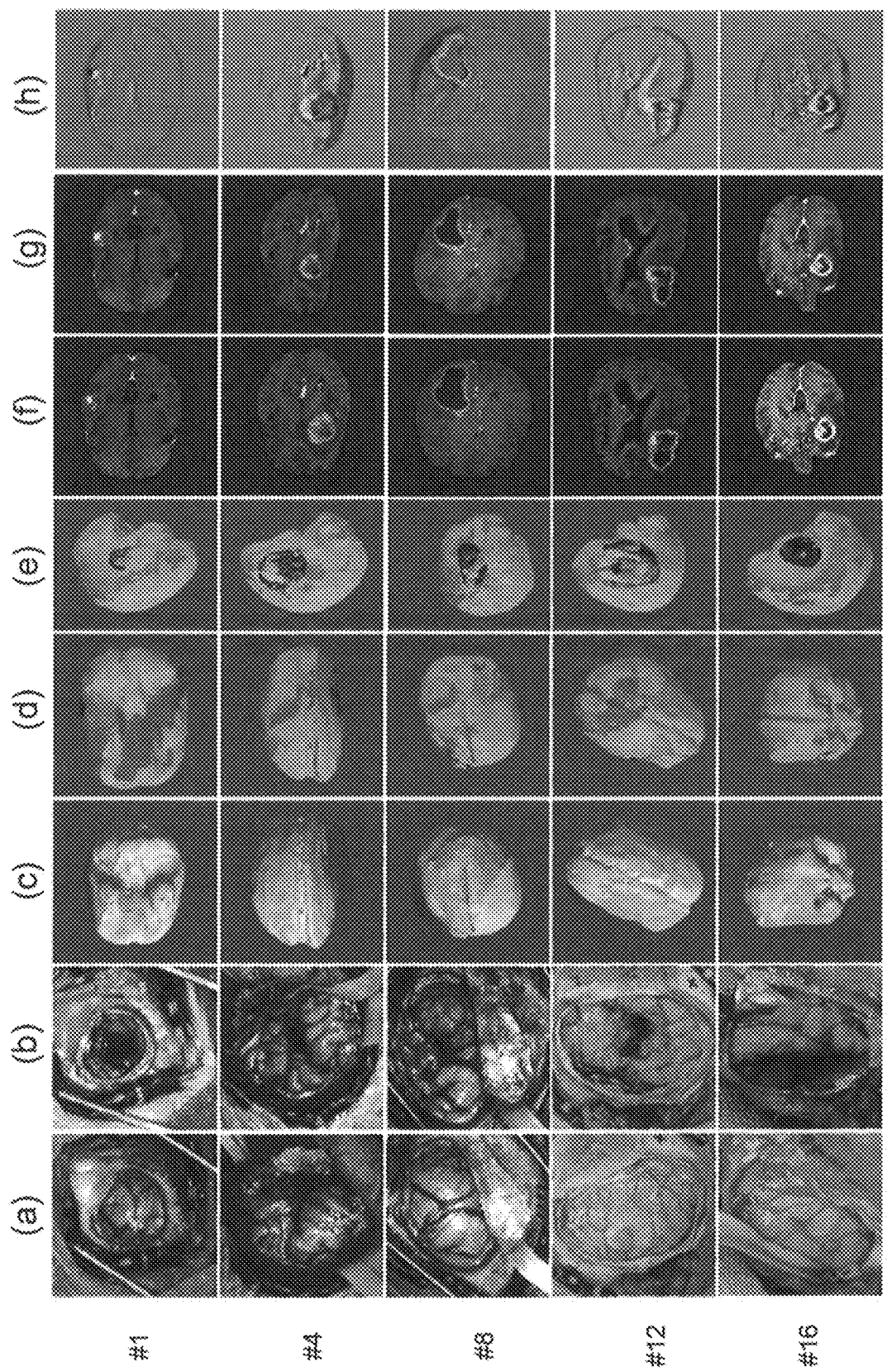
FIG. 12B schematically shows quantitative visualizations of the patients #1, #4, #8, #12 and #16 listed in FIG. 12A according to certain embodiments of the present invention.

FIG. 12B schematically shows quantitative visualizations of the patients #1, #4, #8, #12 and #16 listed in FIG. 12A according to certain embodiments of the present invention. In particular, as shown in FIG. 12B, (a) shows pre-resection BMP, (b) shows post-resection BMP, (c) shows brain shift as observed with overlay of deformed (white) and undeformed (red) brain mesh, (d) shows a top view, (e) shows overlay of deformed mesh w/post-resection LRS, (f) shows an original MR image, (g) shows a deformed MR image, and (h) shows a difference image.

As shown in FIG. 12B($a$), for each of the patients, the pre-resection BMP as shown in the first column includes a 3D textured point cloud of the cortical surface prior to resection, which is representative of the data one could achieve with the invention herein and again done without the use of tracking technologies. As shown in FIG. 12B($b$), for each of the patients, the post-resection BMP as shown in the second column includes the 3D textured point cloud after some resection has taken place. The remaining columns (c) to (g) as shown in FIG. 12 are concerned with demonstrating the 3D correction aspects associated with this particular embodiment. More specifically, while only cortical surface measurements are made to monitor deformation using the trackerless approach, the data can in fact be used to drive a fully 3D correction to localization, not just the surface.

Figure 13:
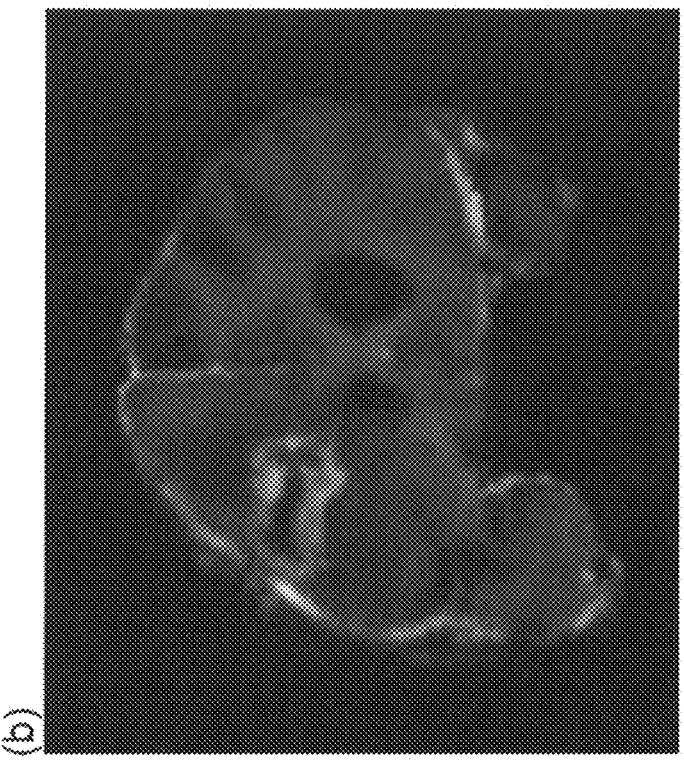
FIG. 13 schematically shows subsurface validation of a patient according to certain embodiments of the present invention, where (a) shows no correction, and (b) shows correction.
Figure 13:
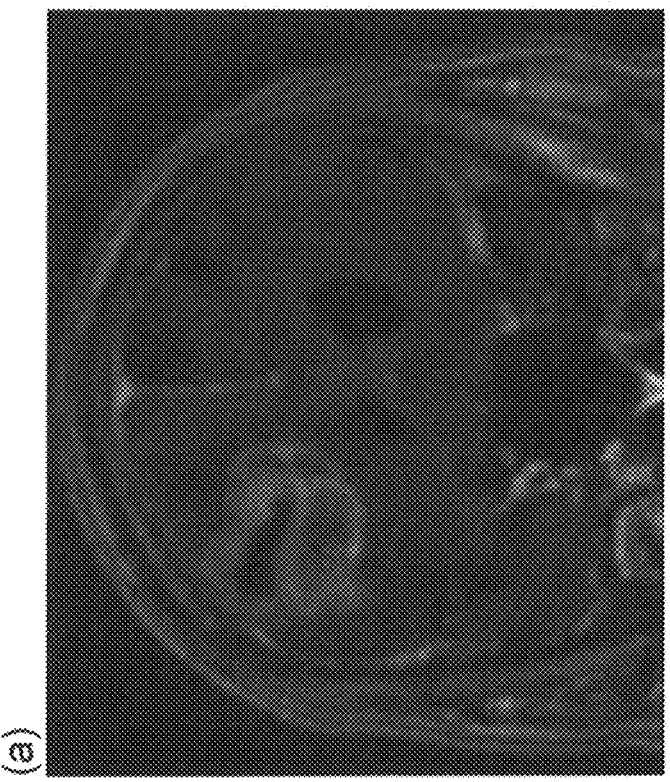

FIG. 13 schematically shows subsurface validation of a patient according to certain embodiments of the present invention, where (a) shows no correction, and (b) shows correction. As shown in FIG. 13, the red dot is the intraoperative designation of extent of resection as acquired with a conoprobe swabbing of the resection cavity after resection completed, which should be at the margin of the tumor to designate its edge. Specifically, FIG. 13($a$) shows a cross-section using standard soft-tissue image guided surgery techniques that utilize standard image guided surgery techniques (namely rigid image-to-physical registration). FIG. 13($b$) shows the subsurface validation of a patient applied with the soft-tissue deformation corrected guidance system according to certain embodiments of the present invention. As shown in FIG. 13($b$), the conoprobe red dot is now localized at the edge of the enhancing legion. This indicates that the resection margin localized with the conoprobe intraoperatively is in fact at the edge of the lesion itself. It was found in post-operative scans that the resection performed was radiologically clear of tumor. In comparison, FIG. 13($a$) shows that inferior to the red dot location, there is substantial inferior tumor remaining when the postoperative results indicated the patient was radiologically clear of tumor. Using FIG. 13($a$) for guidance could inspire the surgeon to resect more brain tissue (in this case healthy tissue), whereas FIG. 13($b$) would indicate not to do so, arguably a more accurate result based on postoperative findings.

In certain embodiments, the method and system as disclosed above may be used for performing trackerless image guided soft tissue surgery to a patient. In certain embodiments, an image guidance framework may be used to perform the method as described above.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

LIST OF REFERENCES

[1]. Skrinjar O, Tagare H, Duncan J. Surface growing from stereo images. Computer Vision and Pattern Recognition, 2000 Proceedings IEEE Conference on2000. p. 571-6 vol. 2.
[2]. Clarkson M J, Rueckert D, King A P, Edwards P J, Hill D L G, Hawkes D J. Registration of video images to tomographic images by optimising mutual information using texture mapping. Medical Image Computing and Computer-Assisted Intervention, Miccai'99, Proceedings1999. p. 579-88.
[3]. Edwards P J, King A P, Maurer C R, de Cunha D A, Hawkes D J, Hill D L G, et al. Design and evaluation of a system for microscope-assisted guided interventions (MAGI). Medical Image Computing and Computer-Assisted Intervention, Miccai'99, Proceedings1999. p. 842-51.
[4]. K. Sun, T. S. Pheiffer, A. L. Simpson, J. A. Weis, R. C. Thompson, and M. I. Miga, "Near real-time computer assisted surgery for brain shift correction using biomechanical models," *IEEE Journal of Translational Engineering in Health and Medicine*, Vol. 2, 2014.
[5]. I. Chen, et. al, "Intraoperative brain shift compensation: Accounting for dural septa," IEEE Transactions on Biomedical Engineering, Vol. 58, No. 3, pp. 499-508, 2011.
[6]. A. L. Simpson, T. S. Pheiffer, D. Caleb Rucker, A. K. Sills, K. Sun, R. C. Thompson, and M. I. Miga, 'Evaluation of conoscopic holography for estimating tumor resection cavities in model-based image-guided neurosurgery', IEEE Transactions on Biomedical Engineering, Vol. 61, No. 6, pp. 1833-1843, 2014.

What is claimed is:

1. A method for performing trackerless image guided soft tissue surgery on a living subject, comprising:
   (a) performing pre-operative preparation for the living subject, comprising:
      generating a first three-dimensional textured point cloud (TPC) for a surface of the living subject covering an organ, wherein the organ is formed by the soft tissue, comprising placing a plurality of first markings on the surface of the living subject;
      scanning at least one field of view (FOV) image of the surface of the living subject with the first markings;
      constructing the first three-dimensional TPC based on the at least one FOV image using principles of computer vision;
      registering the first three-dimensional TPC to a magnetic resonance (MR) model of the organ to generate a fused three-dimensional TPC-to-MR display visibly relating the FOV of the surface of the living subject as represented by the TPC to the MR image volume used for surgery planning; and
      performing an entry-into-body plan on the surface using the fused three-dimensional TPC-to-MR display, wherein the fused three-dimensional TPC-to-MR display is provided as an initial MR-to-patient alignment;
   (b) performing an intra-operative cortical surface registration to the MR model, comprising:
      opening the surface based on the entry-into-body plan to expose a cortical surface of the organ;
      capturing at least one FOV image of the cortical surface of the organ with a plurality of second markings, wherein the second markings are visible in the at least one FOV image of the cortical surface of the organ;
      generating a second three-dimensional TPC for the cortical surface of the organ based on the at least one FOV image of the cortical surface of the organ; and
      performing an MR-to-cortical surface alignment by registering the second three-dimensional TPC to the MR model to generate an intra-operatively fused three-dimensional TPC-to-MR display visibly relating the FOV of the cortical surface of the organ for shift measurement and compensation; and
   (c) performing the shift measurement and compensation to the MR model of the organ, comprising:
      performing absolute deformation measurement of the organ based on the second markings maintaining a fixed reference to the living subject subsequent to the MR model with the cortical surface registration;
      obtaining shift correction to the MR model using the absolute deformation measurements; and
      adjusting an image guidance system (IGS) based on the shift correction for performing an operation to the organ,
   wherein the method is performed without a separate optical tracking device.

2. The method of claim 1, wherein the organ is a brain, the surface is a scalp surface of the living subject, and the entry-into-body plan is a craniotomy plan.

3. The method of claim 1, wherein the step of scanning at least one FOV scanned image is performed by a stereo camera, a stereovision device, or a stereo-pair or laser scanning device.

4. The method of claim 1, wherein the first markings are ink markings or geometrically distinct marking objects printed or adhered on the rigid surface of the living subject, and the second markings are implants or soft-designated-visible dots adhered to a rigid bone surface of the organ, unique geometric reference targets on the bone or cortical surface of the organ, or a combination of them.

5. The method of claim 4, wherein the step (a) further comprises:
   performing segmentation and building the MR model; and
   constructing a pre-operatively determined distribution of possible brain deformations based on a computational model.

6. The method of claim 5, further comprising:
   performing an intra-operative post-resection cortical surface TPC and comparing the post-resection cortical surface TPC to a pre-resection cortical surface TPC taken before resection;
   performing registration of the post-resection and pre-resection cortical surface TPCs using the second markings; and
   once the post-resection and pre-resection cortical surface TPCs are placed in a same reference, determining shift measurement of corresponding features on the post-resection and pre-resection cortical surface TPCs, and using the determined shift measurement to drive deformation compensation of the MR model using the computer model.

7. A method for performing trackerless image guided soft tissue surgery on a living subject, comprising:
(a) performing at least one image-to-physical registration to the living subject, comprising:
(1) performing a pre-operative registration to an organ of the living subject wherein the organ is formed by the soft tissue, comprising:
generating a first three-dimensional textured point cloud (TPC) for a surface of the living subject covering the organ by placing a plurality of first markings on a surface of the living subject;
scanning at least one field of view (FOV) image of the surface of the living subject with the first markings;
constructing the three-dimensional TPC based on the at least one FOV image using principles of computer vision; and
registering the first three-dimensional TPC to a magnetic resonance (MR) model of the organ to generate a fused three-dimensional TPC-to-MR display visibly relating the FOV of the surface of the living subject as represented by the TPC to the MR image volume used for surgery planning;
performing an entry-into-body plan on the surface using the fused three-dimensional TPC-to-MR display, wherein the fused three-dimensional TPC-to-MR display is provided as an initial MR-to-patient alignment; and
(2) performing an intra-operative cortical surface registration to the MR model for a MR-to-cortical surface alignment, comprising:
opening the surface based on the craniotomy plan to expose a cortical surface of the organ;
capturing at least one FOV image of the cortical surface of the organ with a plurality of second markings, wherein the second markings are visible in the at least one FOC image of the cortical surface of the organ;
generating a second three-dimensional TPC for the cortical surface of the organ based on the at least one FOV image of the cortical surface of the organ; and
performing the MR-to-cortical surface alignment by registering the second three-dimensional TPC to the MR model to generate an intra-operatively fused three-dimensional TPC-to-MR display visibly relating the FOV of the cortical surface of the organ for absolute deformation measurement;
(b) performing the absolute deformation measurement of the organ of the living subject based on the second markings maintaining a fixed reference to the living subject subsequent to the at least one image-to-physical registration;
(c) performing shift correction to the organ using the absolute deformation measurements; and
(d) adjusting an image guidance system (IGS) based on the shift correction for performing operation to the organ,
wherein the method is performed without a separate optical tracking device.

8. The method of claim 7, wherein the step (1) further comprises:
performing segmentation and building the MR model; and
constructing a pre-operative atlas.

9. The method of claim 7, wherein the step of scanning at least one FOV scanned image is performed by a stereo camera, a stereovision device, or a stereo-pair or laser scanning device.

10. The method of claim 7, wherein the first markings are ink markings or geometrically distinct marking objects printed or adhered on the surface of the living subject.

11. The method of claim 7, wherein the organ is a brain, the surface is a scalp surface of the living subject, and the entry-into-body plan is a craniotomy plan.

12. The method of claim 7, wherein the step (a) further comprises:
performing an intra-operative post-resection registration to the MR model.

13. The method of claim 7, wherein the second markings are implants or soft-designated-visible dots adhered to a rigid bone surface of the organ, unique geometric reference targets on the bone or cortical surface of the organ, or a combination of them.

* * * * *